(12) United States Patent
Dang et al.

(10) Patent No.: US 9,200,998 B2
(45) Date of Patent: Dec. 1, 2015

(54) METHOD AND APPARATUS FOR ELLIPSOMETRY MEASUREMENT

(75) Inventors: Jiang-tao Dang, Shanghai (CN); Ningning Pan, Shanghai (CN); Haijun Gao, Shanghai (CN)

(73) Assignee: RAINTREE SCIENTIFIC INSTRUMENTS (SHANGHAI) CORPORATION, Shanghai (CN)

( * ) Notice: Subject to any disclaimer, the term of this patent is extended or adjusted under 35 U.S.C. 154(b) by 526 days.

(21) Appl. No.: 13/061,878

(22) PCT Filed: Sep. 3, 2009

(86) PCT No.: PCT/CN2009/073713
§ 371 (c)(1),
(2), (4) Date: Mar. 2, 2011

(87) PCT Pub. No.: WO2010/025672
PCT Pub. Date: Mar. 11, 2010

(65) Prior Publication Data
US 2011/0176133 A1 Jul. 21, 2011
US 2012/0038920 A2 Feb. 16, 2012

(30) Foreign Application Priority Data
Sep. 3, 2008 (CN) .......................... 2008 1 0042435

(51) Int. Cl.
*G01N 21/21* (2006.01)
*G01N 21/27* (2006.01)

(52) U.S. Cl.
CPC ............ *G01N 21/211* (2013.01); *G01N 21/274* (2013.01)

(58) Field of Classification Search
CPC ........................... G01N 21/211; G01N 21/274
USPC .......................................................... 356/369
See application file for complete search history.

(56) References Cited

U.S. PATENT DOCUMENTS

| 4,053,232 | A | * | 10/1977 | Dill et al. | 356/369 |
| 4,906,844 | A | * | 3/1990 | Hall | 250/225 |
| 5,042,951 | A | * | 8/1991 | Gold et al. | 356/369 |
| 5,076,696 | A | * | 12/1991 | Cohn et al. | 356/369 |
| 5,728,494 | A | * | 3/1998 | Kawano et al. | 430/5 |
| 5,831,733 | A | * | 11/1998 | de Groot | 356/369 |
| 5,835,220 | A | * | 11/1998 | Kazama et al. | 356/369 |
| 5,900,939 | A | * | 5/1999 | Aspnes et al. | 356/369 |
| 7,492,455 | B1 | * | 2/2009 | Johs et al. | 356/369 |
| 2002/0097406 | A1 | * | 7/2002 | Fielden et al. | 356/630 |
| 2012/0070065 | A1 | * | 3/2012 | Balak et al. | 382/145 |

* cited by examiner

*Primary Examiner* — Gregory J Toatley
*Assistant Examiner* — Hina F Ayub
(74) *Attorney, Agent, or Firm* — Finnegan, Henderson, Farabow, Garrett & Dunner LLP

(57) ABSTRACT

Methods and systems are provided to avoid the rotation action with the polarizer and the analyzer in complex ellipsometric measurement and repeated processes. In particular, methods and systems are provided which polarize the incident light in a fixed azimuthal angle then illuminate the polarized light onto the target surface, analyze the surface polarized characteristics light in a fixed azimuthal angle, and obtain the light intensity and phase information corresponding to the target surface. Then, based on the relationship between the characteristic information detected by electromagnetic wave and the light intensity information, the disclosed methods and systems obtain the characteristic information of the target surface.

14 Claims, 8 Drawing Sheets

METHOD AND APPARATUS FOR ELLIPSOMETRY MEASUREMENT

FIELD OF THE INVENTION

This application generally relates to optical measurement methods, and more particularly relates to measuring methods and apparatuses utilizing ellipsometric techniques on semiconductor devices and wafer surfaces and other materials.

DESCRIPTION OF THE BACKGROUND ART

The ellipsometric technique is a powerful multi-functional light division technology, used to obtain characteristics information about target surfaces by detecting electromagnetic waves. The characteristics information may include reflectivity, thickness, refractive index, extinction parameters, polarization, surface microstructure, particles, defects, and roughness of the target surface or the thin film surface, and so on. Because the ellipsometric technique is a highly sensitive, non-destructive, and no-contact measurement technique, it is widely used in a variety of fields from basic research to industrial applications, including semiconductor physics, microelectronics, and various areas of biology.

Existing ellipsometric measurement technology works as follows: A light source emits light which passes through a first polarizing plate (often called the polarizer) to generate a polarized light. Then the polarized light illuminates a target surface. The polarized light changes its polarization state after interacting with the target surface. The light then passes through a second polarizer (often called the analyzer), and then enters a detecting device. The ellipsometric technology analyzes light intensity, phase, and polarization states of the light reflected by the target samples, and accordingly obtains the characteristics information that is detected by the electromagnetic waves as they interact with the target surface. This technique works even if the thickness of the target is shorter than the wavelength of the detecting light, e.g., a thickness that is equal or even less than a single atomic layer.

In general, ellipsometry is a technique based on light mirror reflection, in which the incident angle is equal to the reflection azimuthal angle, and the incident light path and the reflected light path are in the same plane (called the incident plane). In the text to follow, the components of the electric field of the polarized light that are parallel with and perpendicular to this incident plane are respectively defined as "p" and "s" components of the polarized light. The polarization state of the polarized light upon interaction with the target surface can change due to various mechanisms, including reflection, transmission, diffraction, and so on. In this application, without loss of generality, the main conditions for reflection are introduced. Because in existing ellipsometry techniques, each measurement can only obtain one set of experimental data, these techniques generally use a rotating ellipsometry method. According to this method, a first motor rotates the polarizer to change the polarizer's azimuthal angle. Similarly, a second motor rotates the second polarizer (the analyzer) to change the analyzer azimuthal angle. Based on all the polarizer azimuthal angles, a set of data can be obtained, and accordingly the characteristics of the target surface can be determined. Therefore, since the existing techniques require a set of data, these techniques suffer some shortcomings, such as long data measuring time, method complexity, and expensive hardware.

SUMMARY OF THE INVENTION

Various embodiments address problems, such as long time data measuring, complex measuring method and expensive measuring hardware caused by rotating the polarizer. In various embodiments, the ellipsometric technique polarizes the light from the light source in a certain azimuthal angle, and then the polarized light is directed onto the target surface. After being reflected by the target surface, the light characteristics could be interpreted based on some relationship information. Finally, based on the obtained light intensity of the reflected light, the characteristics information of the target surface could be determined. In the traditional systems, when conducting the measurement, there always exist deviations in the polarized azimuthal angle, the incident angle, and the analyzed azimuthal angle. To avoid such deviation, various embodiments provide a reference surface for calibration before the measurement for the target surface's characteristics begins.

BRIEF DESCRIPTION OF THE DRAWINGS

In the following detailed description, the character, target, and advantages will be shown better. In the drawings, same or similar drawings stand for same or similar steps or units or devices.

DETAILED DESCRIPTIONS OF THE PREFERRED EMBODIMENTS

Based on FIGS. 1 to 10, the following detailed description describes several embodiments.

First Embodiment

Figure 1:
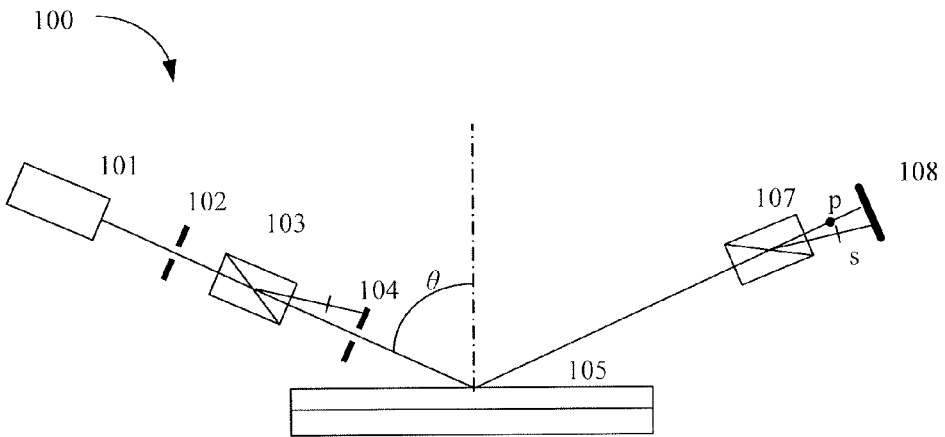
FIG. 1 shows a light division ellipsometry system based on surface reflection in accordance with an embodiment.

FIG. 1 shows a light division ellipsometry system 100 based on surface reflection in accordance with the first embodiment. The system includes a light source 101, a first condenser hole 102, a polarizer 103 (at azimuthal angle 45 degrees), a second condenser hole 104, a target surface 105, an analyzer device 107, and a detection-processing device 108. Also, in system 100, detection-processing unit 108 is connected to a computing device and a calibration device, which are not shown in FIG. 1.

In FIG. 1, the azimuthal angle of polarizer 103 is 45 degrees, and the azimuthal angle of analyzer 107 is 0 degrees. Consistent with an embodiment, target surface 105 may be a $SiO_2$ film. Detection-processing unit 108 receives the output of analyzer 107, namely, p and s components of the light, and detects the light intensity information to obtain the p and s components and the phase relationship between the components. Moreover in FIG. 1, polarized light incident angle θ is near the target surface Brewster azimuthal angle.

Consistent with an embodiment, light source 101 may be a He—Ne laser for which the output wavelength is 632.8 nm. However, light source 101 can use other types of light sources as known by persons of ordinary skill in the art, for example, high-power red LED light sources.

In FIG. 1, first condenser hole 102 is used to better focus the incident light, and hole 104 is used to avoid partial outputs from other polarized light beams into the measurement light path. Use of holes 102 and 104 improves the accuracy of measurement. However, as understood by persons of ordinary skill in the art, hole 102 or hole 104 is not necessary to implement embodiments.

Figure 2:
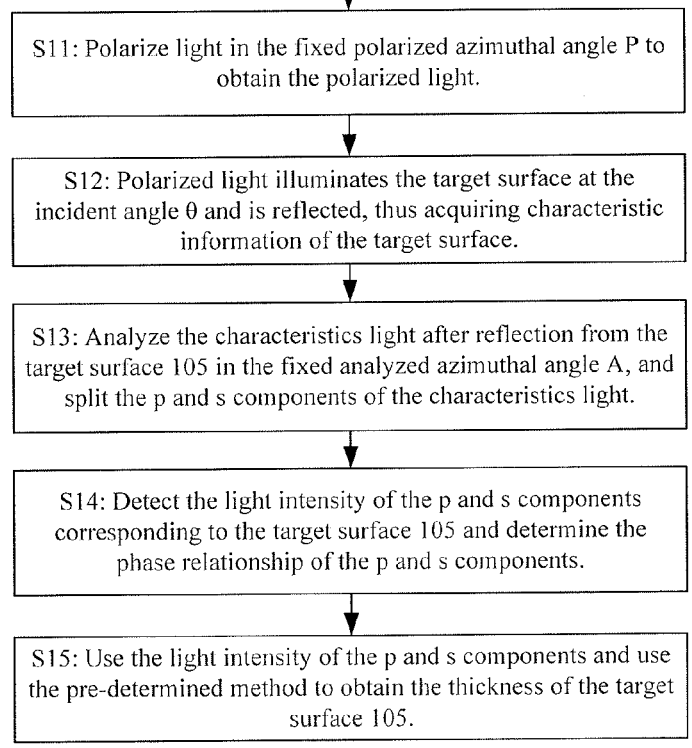
FIG. 2 illustrates a method of ellipsometric measurement in accordance with an embodiment.

FIG. 2 illustrates a method 200 of ellipsometric measurement in accordance with an embodiment. The method 200 may be performed on a target surface $SiO_2$ film, as further described in relation to FIGS. 2, 3a, and 3b. Consistent with an embodiment, a characteristic of the target surface is the thickness of the target. The light source 101 emits light, the emitted light goes through condenser hole 102 and is focused by hole 102 and then illuminates polarizer 103.

In step S11, polarizer 103 polarizes a single wavelength light at a fixed polarizer azimuthal angle P to generate a single wavelength polarized light.

Then, the polarized light goes through second condenser hole 104. Second condenser hole 104 only allows one polarized light passed through polarizer 103, and blocks the rest of polarized lights in order to avoid their impact on the measurement.

In step S12, the polarized light is incident at the incident angle θ onto target surface 105. As known by persons of ordinary skill in the art, without second condenser hole 104, the light path of the polarized light passed through polarizer 103 may be quite different from the light path of the polarized light passed through second condenser hole 104 as shown in FIG. 1. However, in the first case, the additional light will not be reflected by target surface 105 and thus will not reach analyzer device 107. So, the effect to the measurement result can be ignored or even this effect will not be generated. Thus, as mentioned above, second condenser hole 104 is not necessary.

The illuminated polarized light is reflected by target surface 105 and reaches analyzer 107. After the reflection, the nature of the polarized light changes due to the target surface 105, and acquires the characteristic information of the target surface. In the step S13, analyzer 107 analyzes the characteristics light reflected by the target surface 105 in the fixed analyzer azimuthal angle A. Analyzer 107 separates the p component and the s component of the characteristic light and provides them to the detection-processing device 108.

In step S14, detection-processing device 108 receives and detects the light intensity of the p component and the s component of the characteristics light, obtains light intensity information corresponding to the target surface 105, and obtains the phase difference between the p component and the s component. Detection-processing device 108 provides the obtained light intensity information to calculation device 109, which has an electromagnetic connection with the detection-processing device 108 and is not shown in FIG. 1. Specifically, detection-processing device 108 may include a light intensity detecting device and a processing device, wherein the light intensity detecting device is used to detect the light intensity of the p component and the s component of the detected characteristics light, and the processing device is used to obtain the phase difference between the p component and the s component. The processing device may be a micro processing device, executing appropriate programs to calculate the phase difference information. The processing device may include firmware, ASIC, or DSP devices. The specific method of detection of light intensity and calculation of p and s components of the phase component is known to persons of ordinary skill in the art.

Finally, in step S15, calculating device 109 determines the thickness of the target surface 105 based on the light intensity of the p and s components of the characteristic light. As can be understood by persons of ordinary skill in the art, there are several ways to determine the thickness information, not limited by ways shown in this embodiment. Consistent with an embodiment, the principles of the determination are as follows.

The basic formula for the intensity of the output light after passing through polarizer 103 and analyzer 107 is, $$I_{out}(P, A) = \begin{pmatrix} 1 + \\ \dfrac{\tan^2\Psi - \tan^2 P}{\tan^2\Psi + \tan^2 P}\cos 2A + \\ \dfrac{2\tan\Psi\tan P\cos\Delta}{\tan^2\Psi + \tan^2 P}\sin 2A \end{pmatrix} \quad (1)$$

In equation (1), P=π/4, A=0, π/2, tan Ψ is the amplitude ratio of the p and s components of the light, and Δ is the phase difference between the p and s components of the characteristics light. Light intensities $I_{out}(\pi/4,0)$ and $I_{out}(\pi/4,\pi/2)$ can be used to calculate the Fourier coefficient $$\alpha = \frac{\tan^2\Psi - 1}{\tan^2\Psi + 1},$$

and to further calculate the ellipsometry parameters tan Ψ, that is:

$$\alpha = \frac{I(\pi/4, 0)_{out} - I(\pi/4, \pi/2)_{out}}{I(\pi/4, 0)_{out} + I(\pi/4, \pi/2)_{out}} \quad (2)$$

$$\tan\Psi = \frac{I(\pi/4, 0)_{out}}{I(\pi/4, \pi/2)_{out}}$$

Moreover, $$\beta = \frac{2\tan\Psi\cos\Delta}{\tan^2\Psi + 1}$$

is the first-order Fourier coefficient of the output light intensity.

Figure 3A:
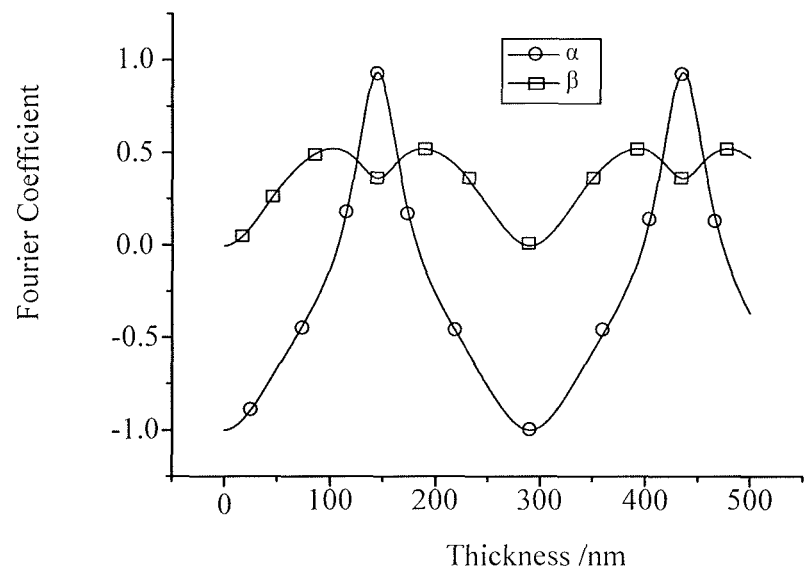
FIG. 3a shows variations of the Fourier coefficients as a function of the thickness of the target in accordance with an embodiment.

In various embodiments, variation of the Fourier coefficients as a function of the thickness of the target can be determined in advance. FIG. 3a shows the results of such determination in accordance with an embodiment. In FIG. 3a, the angle θ is 75.55 degrees, and the light source 101 is a He—Ne laser and outputs light with wavelength 632.8 nm. FIG. 3a, shows variations in the Fourier coefficients as functions of thickness of the surface, when the thickness of the surface changes in the range of 0 to 500 nm. As seen in FIG. 3a, the Fourier coefficients are periodic functions of the surface thickness.

Figure 3B:
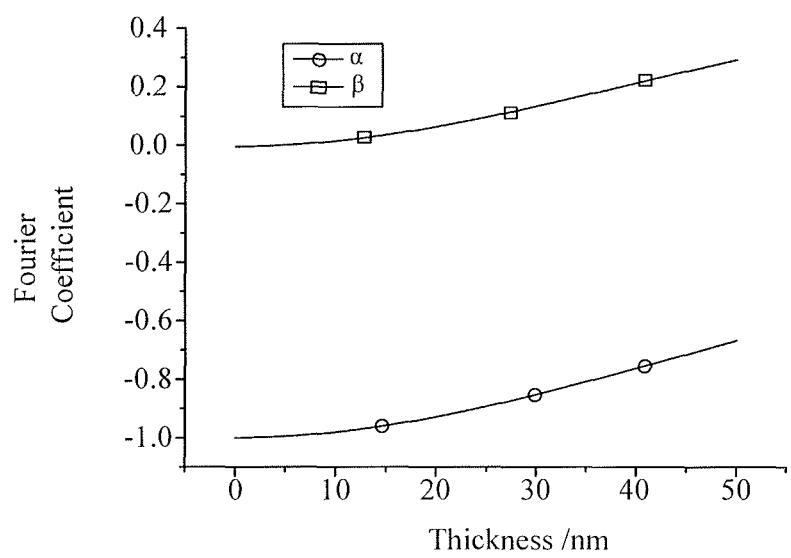
FIG. 3b shows variations of the Fourier coefficients as a function of the thickness of the target in accordance with an embodiment.

FIG. 3b shows the variations in the Fourier coefficients when the wavelength of the output light is 632.8 nm, the incident angle of the polarized light is 75.55 degrees, and when the thickness of the surface varies in the range of 0 to 50 nm. FIG. 3b shows that when the thickness is within 0 to 50 nm, the Fourier coefficient is a monotonic function of the surface thickness.

Figure 4A:
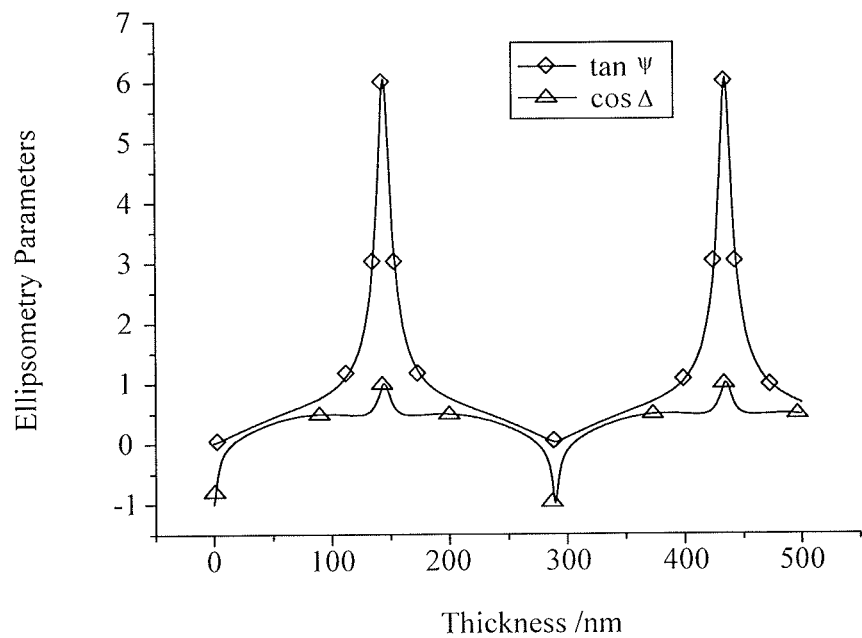
FIG. 4a shows the variations in ellipsometry parameters as a function of the thickness of the target in accordance with an embodiment.

FIG. 4a shows the variations in the ellipsometry parameters tan Ψ and Cos(Δ) as a function of the thickness of the target. In FIG. 4a, the wavelength of the output light is 632.8 nm, the incident angle of the polarized light is 75.55 degrees, and the thickness of the surface varies in the range of 0 to 500 nm. FIG. 4a shows that when the thickness varies between 0 and 500 nm, the ellipsometric parameters tan Ψ and Cos(Δ) vary as periodic functions of the surface thickness.

Figure 4B:
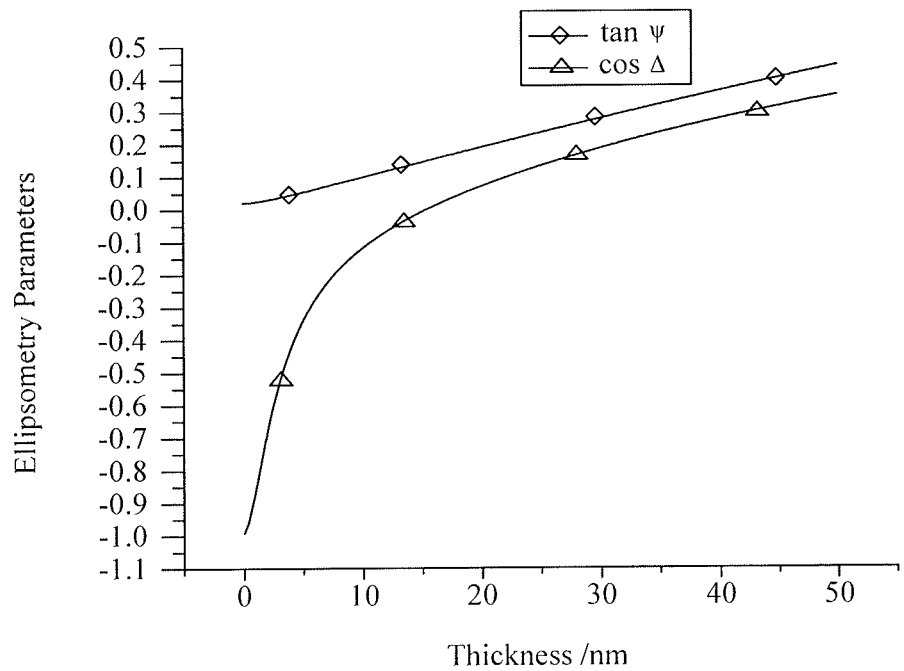
FIG. 4b shows the variations in ellipsometry parameters as a function of the thickness of the target in accordance with an embodiment.

FIG. 4b shows the variations of the ellipsometry parameters tan Ψ and Cos(Δ) as a function of the thickness of the target, when the wavelength of the output light is 632.8 nm, the incident angle of the polarized light is 75.55 degrees, and when the thickness of the surface varies in the range of 0 to 50 nm. FIG. 4b shows that, when the thickness is within the range 0 to 50 nm, the ellipsometry parameters tan Ψ and Cos(Δ) are monotonic functions of the surface thickness.

During the measurement process, the Fourier coefficient can be calculated based on equation (2). When all the azimuthal angles, including the polarized azimuthal angle, analyzer azimuthal angle, and the incident angle between the polarized light and the target surface are determined, and when the wavelength of the laser and also the refractive index of the target surface are known, all the Fourier coefficients α,β are thus known. Thus a control method can be used to find the specific Fourier coefficient within the range of values from the known Fourier coefficients that is most similar to the measured Fourier coefficients. Accordingly, the thickness of the target surface can be deduced to be equal to the thickness corresponding to the specific Fourier coefficient.

In theory, the Fourier coefficients α,β are functions of the thickness, the polarized light incident angle θ, the wavelength, light constants of the material of the target surface, the polarizer azimuthal angle and the analyzer azimuthal angle. In particular, the thickness, the polarized light incident angle θ, the wavelength, and light constants of the material of the target surface affect the ellipsometry parameters and the ellipsometry parameters in turn affect the Fourier coefficients. When using a fixed wavelength light source, and because the light constants of the material are fixed, their effects on the measurement can be ignored. Thus, the thickness of the target surface is the only factor that determines the Fourier coefficients α,β. Based on this principle, in a single range, Fourier coefficients vary with the thickness and each Fourier coefficient is a monotonic function of the thickness. Thus, according to the relationship between the Fourier coefficients and the thickness, the thickness can be calculated.

This exemplary embodiment describes the relationship between the Fourier coefficients and the ellipsometry parameters and the thickness when the light source 101 outputs light with the wavelength 632.8 nm, and the incident angle of the polarized light is 75.55 degrees. As is widely understood by the persons of ordinary skill in the art, when the light wavelength and the incident angle are different, the relationship will change between the Fourier coefficients α,β on the one hand, and the ellipsometry parameters and the thickness on the other hand, but the principles of this disclosure will still be applicable.

Because, in addition to being related to the thickness of the target surface, each Fourier coefficient has a one-to-one relationship with the reflectivity, refractive index, extinction coefficient, polarization, surface microstructure, particles, defects and other surface roughness features as well, the methods of this disclosure are not limited to finding the thickness of the target surface, and other characteristics of the surface can also be measured. Persons of ordinary skill in the art can understand that methods and systems of this disclosure can also used to measure other kinds of target surfaces and their characteristic information. Thus, for the sake of brevity, methods are not described for other situations.

The above-described embodiments show the measurement method when the fixed polarized azimuthal angle P and the fixed analyzer azimuthal angle A are all in the ideal state, that is P=π/4, A=0,π/2, and when θ=75.55 degrees. In the process of real measurement, due to the deviation in the measuring device and the light path, this condition is difficult achieve. Thus, when there is a deviation in polarized azimuthal angle, incident angle, or the fixed analyzer azimuthal angle, a calibration action must be taken on the deviation azimuthal angle, to determine the actual fixed polarized azimuthal angle, the incident angle, and the fixed analyzer azimuthal angle and, based on those actual values, to obtain the real thickness of the target surface.

Figure 5:
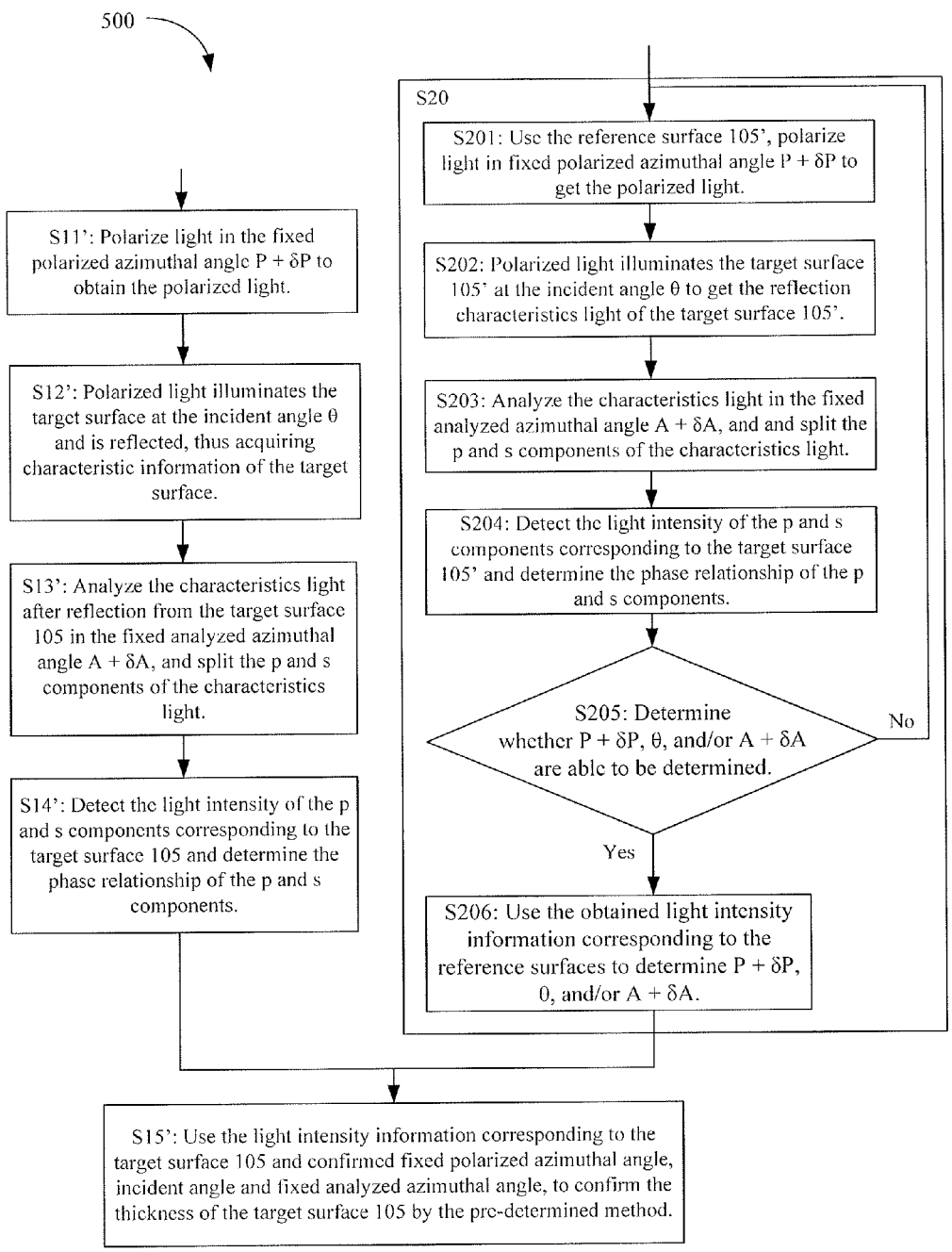
FIG. 5 illustrates a method of ellipsometric measurement, which includes calibration, in accordance with an embodiment.

To perform calibration, the method 500 of measuring the thickness of the target surface, shown in FIG. 5, will also include steps S20. In steps S20, calibration is performed at the fixed polarizer azimuthal angle, the incident angle, and the fixed-analyzer azimuthal angle to obtain the actual values of the fixed polarizer azimuthal angle, the incident angle, and the fixed-analyzer azimuthal angle. The method shown in FIG. 5 also includes the above-described steps S11 to S14, respectively labeled S11' to S14', for determining light intensity information about the p component and s component. Consequently, in step S15', based on the determined light intensity information about the p and s components, and also using the fixed polarizer azimuthal angle, the incident angle and the fixed analyzer azimuthal angle, the thickness of the target surface can be determined.

The calibration process for the polarized azimuthal angle, the analyzer azimuthal angle, and the incident angle shown is shown in FIG. 5 with some reference to FIGS. 1 and 2. Before the calibration, first target surface 105 should be replaced with a reference target surface 105' used for the calibration. Consistent with an embodiment, this reference target surface is preferably a $SiO_2$ film.

The calibration process works as follows. Supposing there is an azimuthal angle deviation between the polarizer and the analyzer, these angles are denoted as P+δP, A+δA, where δP represents the deviation between the actual azimuthal angle and the current theoretical value (e.g., π/4), and where δA represents the deviation between the actual analyzer azimuthal angle A and the current theoretical value (e.g., 0 and π/2). In this case, the output light intensity after passing through polarizer 103 and analyzer 107 is determined by the following equation:

$$I_{out}(P+\delta P, A+\delta A) = I_0 \begin{pmatrix} 1 + \\ \frac{\tan^2\Psi - \tan^2(P+\delta P)}{\tan^2\Psi + \tan^2(P+\delta P)}\cos 2(A+\delta A) + \\ \frac{2\tan\Psi\tan(P+\delta P)\cos\Delta}{\tan^2\Psi + \tan^2(P+\delta P)}\sin 2(A+\delta A) \end{pmatrix} \quad (3)$$

$$= \begin{pmatrix} 1 + \\ \alpha'\cos 2(A+\delta A) + \\ \beta'\sin 2(A+\delta A) \end{pmatrix}$$

$$= \begin{pmatrix} 1 + \\ (\alpha'\cos 2\delta A + \beta'\sin 2\delta A)\cos 2A + \\ (-\alpha'\sin 2\delta A + \beta'\cos 2\delta A)\sin 2A \end{pmatrix}$$

in which, $$\alpha' = \frac{\tan^2\Psi - \tan^2(P+\delta P)}{\tan^2\Psi + \tan^2(P+\delta P)}$$

$$\beta' = \frac{2\tan\Psi\tan(P+\delta P)\cos\Delta}{\tan^2\Psi + \tan^2(P+\delta P)}$$

represents the theoretical Fourier coefficients, and $\Delta$ is the phase difference between the p and s components of the characteristic light.

The theoretical value of the polarized azimuthal angle is $P=\pi/4$, its deviation is $\delta P$, the theoretical value of the analyzer azimuthal angle is $A=0,\pi/2$, and its deviation is $\delta A$. Therefore, the two light intensities are, $$I_1 = I(0) = I_{01}(1+\alpha'\cos 2\delta A + \beta'\sin 2\delta A)$$

$$I_2 = I(\pi/2) = I_{01}(1-\alpha'\cos 2\delta A - \beta'\sin 2\delta A) \quad (4)$$

Based on equation (4), the light intensity can be calculated as: $I_{01} = (I_1+I_2)/2$ After normalization, the intensities are determined as:

$$I_1' = 1+\alpha'\cos 2\delta A + \beta'\sin 2\delta A$$

$$I_2' = 1-\alpha'\cos 2\delta A - \beta'\sin 2\delta A \quad (5)$$

Thus, the objective function is $$X(\vec{t}, \delta P, \theta, \delta A, \vec{n}, \vec{k}, \lambda) = \sum_{i=1}^{2}\sum_{j=1}^{m}\left(I_{ij}' - I_{ij}^{theory}\right)^2 \quad (6)$$

where, $\vec{t}$ is the thickness of the surface, $\theta$ is the incident angle, $\delta P$ is the deviation of the polarizer azimuthal angle of the polarizer 103, $\delta A$ is the deviation of the analyzer azimuthal angle of the analyzer 107, $\vec{n}$ is the refractive index of the reference surface, $\vec{k}$ is the extinction coefficient for the reference surface, and $\lambda$ is the wavelength. In equation (6), $I_{ij}'$ is the normalized obtained light intensity and $I_{ij}^{theory}$ is the theoretically calculated light intensity. Further, in the sums of equation (6), the index i runs over the p and s components, and the index j runs over various the reference surfaces uses for calibration.

Considering the calibration equation (6), supposing that m reference surfaces with different known thicknesses are used for calibration, and that the wavelength of the used light is constant, then $\vec{n},\vec{k}$ will also be constant. Thus X has 2m variables. After removing the linear dependencies among related variables, there remains m variables that could be used. There are 3 unknown variables including the variation in the polarized azimuthal angle $\delta P$, the incident angle $\theta$ and the analyzer azimuthal angle $\delta A$. Using the basic calculating method, all the unknown parameters could be found only when m>3.

If one or more of the variables: polarizer 103, azimuthal angle $P+\delta P$, incident angle $\theta$, and the analyzer azimuthal angle $A+\delta A$ are known, then in the calibration step, remaining variables will be calibrated. Since the number of unknown parameters is high, then the required number of nonlinear equations and then the corresponding measurements on the reference surface time is reduced.

The above description and the related theory explained the principle of the calibration method provided by this disclosure. The following description addresses the steps in the calibration process, with reference to FIGS. 1 and 5:

FIG. 5 shows a flow chart for a light division method for detecting characteristics information of a surface via the electromagnetic waves in accordance with an embodiment. In step S201, polarizer 103 polarizes the light at the fixed polarized azimuthal angle $P+\delta P$ to generate the polarized light. In step S202, the polarized light illuminates the known reference surface 105' at the incident angle $\theta$ and is reflected off the surface as characteristic light. In step S203, analyzer 107 analyzes the characteristic light reflected from the reference surface 105' at a fixed analyzed azimuthal angle $A+\delta A$, and separates the p and s components of the characteristic light. In step S204, detection-processing device 108 detects the light intensity of the p and s components of the characteristics light to obtain one set of light intensity information corresponding to reference surface 105'.

In equation (6), the variables include the thickness of the reference surface $\vec{t}$, the deviation of the fixed polarizer azimuthal angle $\delta P$, the incident angle $\theta$, the fixed polarizer azimuthal angle deviation $\delta A$, the refractive index $\vec{n}$ of the reference surface 105', the light extinction coefficient $\vec{k}$ of the reference surface 105', and the wavelength $\lambda$. Using numerical approximation methods, assuming the light intensity of the detected p and s components and the square of the sum of their corresponding theoretical light intensity deviation to be determined, equation (6) provides a nonlinear equation for finding the thickness of the reference surface 105'.

Still referring to FIG. 5, in step S205, based on the relationship between the foresaid function number and the unknown parameters number, and based on the nonlinear equations corresponding to the target surface 105', it is decided whether it is possible to determine all the unknown parameters, that is, the fixed polarized azimuthal angle $P+\delta P$, the incident angle $\theta$, and the fixed analyzer azimuthal angle $A+\delta A$. If all those unknown parameters could not be determined, the reference surface 105' will be replaced with another reference surface 105'', and steps S201 to S205 will be repeated, until all the above listed unknown parameters, that is, azimuthal angle parameters in the fixed polarized azimuthal angle $P+\delta P$, the incident angle $\theta$, and the fixed analyzer azimuthal angle $A+\delta A$ can be determined by solving a plurality nonlinear equations corresponding to a plurality of reference surfaces.

When it is possible to determine all the unknown parameters according to one or more nonlinear equations corresponding to one or more reference surfaces, the method shown in FIG. 5 moves to steps S206. Based on one or more nonlinear equations corresponding to the one or more reference surfaces, and using the relationships between the light intensity and surface characteristics information, derived from nonlinear optimization theory, all of the unknown parameters are determined, that is, the polarized azimuthal angle P+δP, the incident angle θ, and the fixed analyzer azimuthal angle A+δA are determined.

The calculating method could be the non-linear optimization method L-M, or could be any other method that could analyze the non-linear equations. The detailed calculation method depends on the available method. In some embodiments, the calculation process is performed by the calibration device 110. In some embodiments, the calibration device 110 could be a micro-processor that runs a program to perform the calibration process. Alternatively, in some other embodiments, the calibration device could be a corresponding firmware, ASIC, or DSP devices.

Independent of the above-described steps S201 to S205, and similar to steps S11 to S14 of FIG. 2, the process 500 also includes steps S11' to S14', as shown in FIG. 5. In steps S201 to S206, the light intensities of the p and s components, and the phase relationship information between the p and s component are determined. It is noted that all the azimuthal angles, that is, the fixed polarized azimuthal angle P+δP, the incident angle is θ and the fixed analyzer azimuthal angle A+δA, are the same during the detecting process (steps S11' to S15') and the calibration process (steps S20).

After determining the fixed polarized azimuthal angle P+δP, the incident angle θ, and the fixed analyzer azimuthal angle A+δA, the known light parameters of the reference surface 105', that is, $\vec{n}$ and $\vec{k}$, and the detected azimuthal angle parameters, are inserted into equation (6) and, using the L-M method, the thickness is determined. Other nonlinear functions could also be used to determine the thickness, and the specific method does not change the focus of this disclosure. The calculating process could be completed by the calculating device 109. In various embodiments, calculating device 109 can be a microprocessing device performing the process for conducting the calibration process, or a firmware, ASIC, or DSP devices.

Second Embodiment

In the second embodiment, one or more dividers are installed between the surface and the analyzer along the light path. The one or more dividers divide the characteristics light reflected off the surface. The divided lights are polarized at a fixed azimuthal angle and their light intensities are detected. According to the light intensity of the p and s components of all the divided lights, the characteristic information of the target surface is determined.

Figure 6:
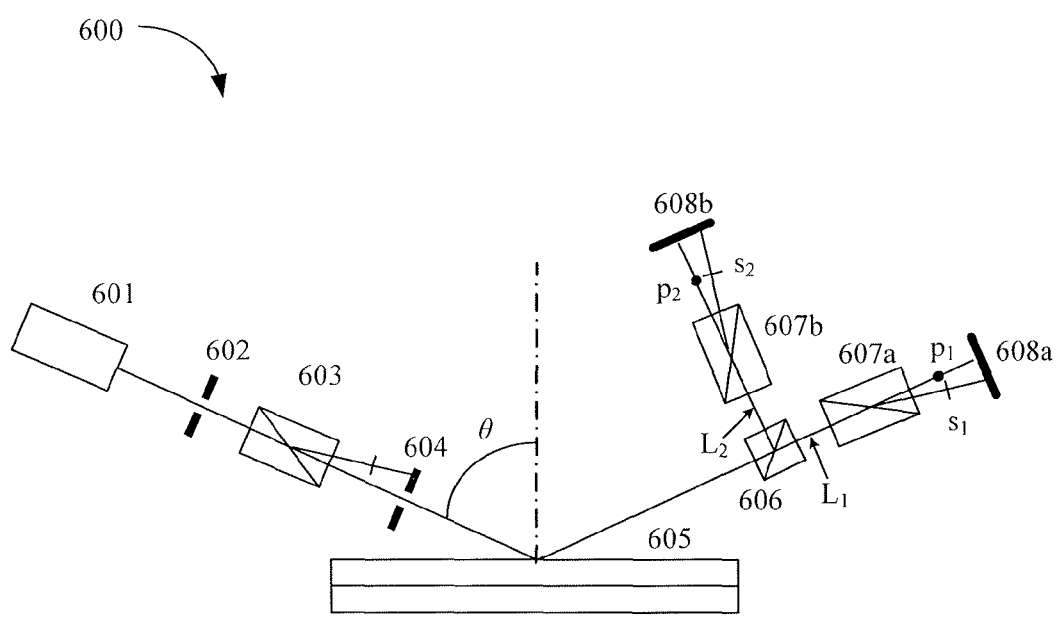
FIG. 6 shows a light division ellipsometric system based on surface reflection for determining the characteristics information in accordance with an embodiment.

FIG. 6 shows a light division ellipsometric system based on surface reflection for determining the characteristic information in accordance to the second embodiment. The system shown in FIG. 6 includes a light source 601, a first condenser hole 602, a polarizer 603 (at an azimuthal angle 45 degrees), a second condenser hole 604, a target surface 605 (preferred to be a SiO₂ film), a light divider 606, a first analyzer device 607a (at an azimuthal angle 0 degrees), and a first detection-processing device 608a. First detection processing device 608a receives the output of first polarizer 607a, wherein the output includes a p-polarized light component and an s-polarized light component, and detects the light intensity information of the s and p components, and also detects the phase relationship between the s and p components. The system in FIG. 6 further includes a second analyzer device 607b (at an azimuthal angle of 45 degrees), and a second detection-processing device 608b. Second detection-processing device 608b receives the output of second polarizer 607b, wherein the output includes a p-polarized light component and an s-polarized light component. Second detection-processing device 608b further detects the light intensity information of the s and p components and the phase relationship between the s and p components. Polarized light incident angle θ is near the target surface Brewster azimuthal angle. Further, in the system shown in FIG. 6, first and second detection-processing units 608a and 608b are connected to a computing device 609 and a calibration device 611, which are not shown in FIG. 6.

In the embodiment shown in FIG. 6, light source 601 uses a He—Ne laser with an output light wavelength of 632.8 nm. As understood by persons of ordinary skill in the art, light source 601 is not limited to the He—Ne laser, and can include other high-power red LED light sources. First condenser hole 602 is used to better focus the incident light. However, as known by persons of ordinary skill in the art, first condenser hole 602 is not necessary to implement the embodiments. Second condenser hole 604 is used the prevent partial output from other polarized light beams into the measurement light path, and thus to avoid the impact of those outputs on the measurement results. Further, as also known by persons of ordinary skill in the art, second condenser hole 604 is also not necessary to implement the embodiments. Usually, the use of first and second condenser holes 602 and 604 help to improve accuracy of the measurements of the surface characteristics information by the electromagnetic waves.

Figure 7:
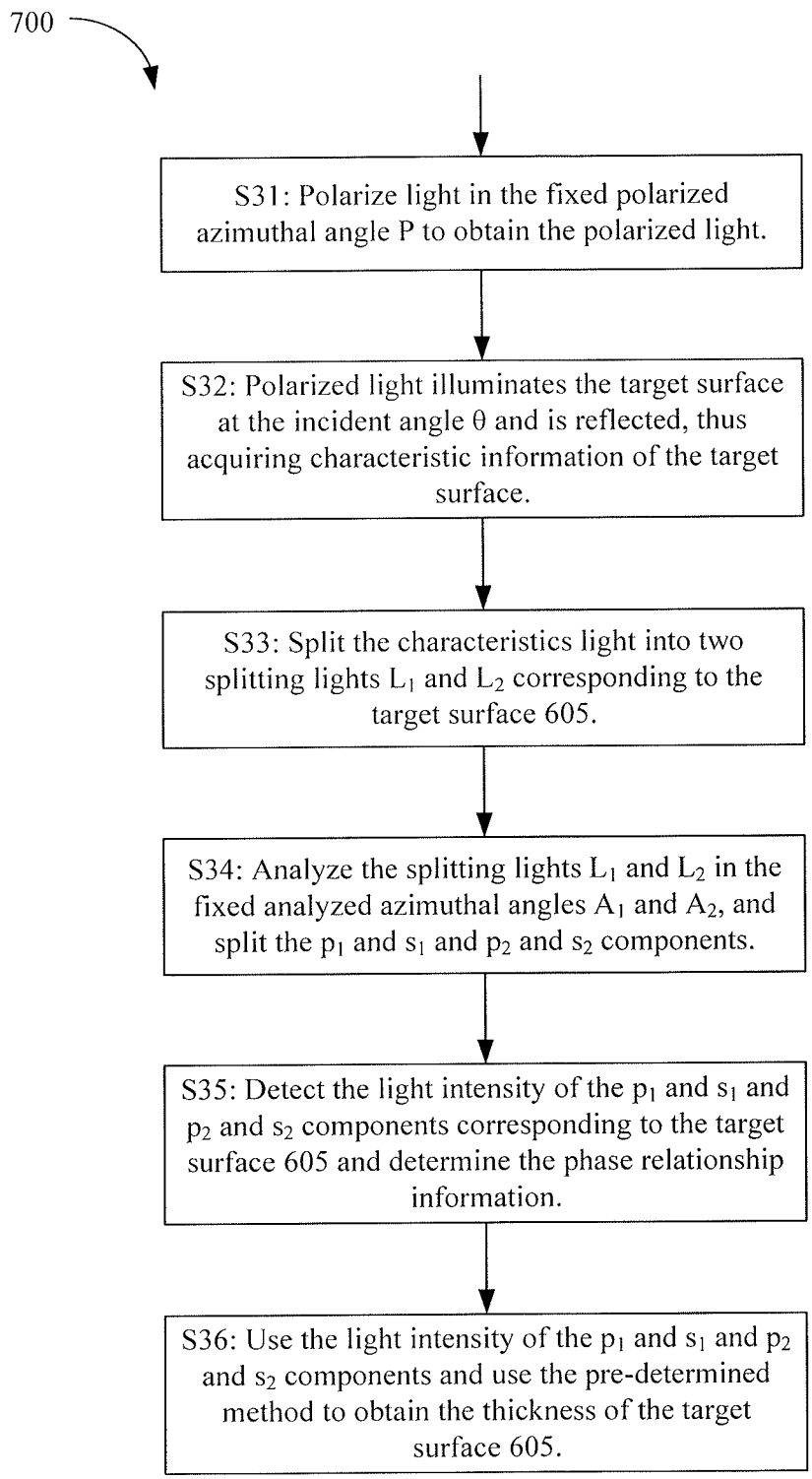
FIG. 7 shows a flow chart for a light division method for detecting characteristics information of a surface via the electromagnetic waves in accordance with an embodiment.

FIG. 7 shows a flow chart for a light division method for detecting characteristics information of a surface via the electromagnetic waves. In particular, the method 700 uses surface reflection and light division ellipsometry techniques, consistent with an embodiment. The following description describes steps of the ellipsometry measurement method for a target surface-SiO₂ film, in relation to FIGS. 6 and 7. That is, in this embodiment, the characteristic information of the target surface is the thickness of the target.

First, at the start of the method, light source 601 emits light, the emitted light goes through first condenser hole 602, is focused hole 602, and then illuminates polarizer 603. In step S31, polarizer 603 polarizes a single wavelength light at a fixed polarizer azimuthal angle P to generate a polarized light. Then, the polarized light goes through second condenser hole 604. Second condenser hole 604 only allows one polarized light passed through polarizer 603, and blocks the rest of polarized lights in order to avoid their impact on the measurement. Thus, in step S32, the polarized light is incident at the incident angle θ onto target surface 605. As known by persons of ordinary skill in the art, without condenser hole 604, the light path of the polarized light pass through polarizer 603 may be quite different from the light path of the polarized light passed through second condenser as shown in FIG. 6. However, in the first case, the additional light will not be reflected by target surface 605 and thus will not reach first and second analyzers 607a and 607b. So the effect to the measurement result can be ignored, or even this effect will not be generated. So, as mentioned above, second condenser hole 604 is not necessary.

The illuminated polarized light is reflected by target surface 605 as a result of which the nature of this polarized light changes. In step S33, light divider 606 divides the characteristics light, which is reflected by the target surface, to generate the corresponding characteristic lights $L_1$ and $L_2$, and then divided light $L_1$ and $L_2$ reach two analyzers 607a and 607b.

In step S34, first analyzer 607a analyzes characteristics light $L_1$ at the fixed analyzer azimuthal angle, separates the $p_1$ and $s_1$ components, which are the p and s component of the $L_1$, and then provides $p_1$ and $s_1$ to second detection-processing device 608a. Second analyzer 607b analyzes characteristics light $L_2$ at the fixed analyzer azimuthal angle, separates the $p_2$ and $s_2$ components, which are the p and s components of light $L_2$, and then provides $p_2$ and $s_2$ to second detection-processing device 608b.

In step S35, first and second detection-processing devices 608a and 608b receive and detect the light intensity of the $p_1$ and $s_1$, and $p_2$ and $s_2$ components, obtain the light intensity information corresponding to the target surface, and obtain the phase difference between the $p_1$ and $s_1$ components, and the phase difference between the $p_2$ and $s_2$ components. First and second detection processing devices 608a and 608b then provide the obtained light intensity information to calculation device 609, which has electromagnetic connections with first and second detection-processing devices 608a and 608b, and is not shown in FIG. 6. Specifically, first and second detection-processing devices 608a and 608b may include light intensity detecting devices and the processing devices, wherein the light intensity detecting device is used to detect the light intensity of the p component and the s component of the detected characteristics lights $L_1$ and $L_2$, and the processing device is used to obtain the phase differences between the p and the s components, $p_1$ and $s_1$ or $p_2$ and $s_2$.

Finally, in step S36, calculating device 609, using the light intensity of the $p_1$ and $s_1$ components and the $p_2$ and $s_2$ components, determines the thickness of the target surface using a predetermined method. It can be understood by persons of ordinary skill in the art that there are several ways to determine the thickness information, and the method is not limited to those detailed in this embodiment. Consistent with an embodiment, the principles of this determination method are as follows.

The basic equation for the intensity of the output light after passing through the polarizer and the analyzer is $$I_{out}(P, A) = I_0\left(1 + \frac{\tan^2\Psi - \tan^2 P}{\tan^2\Psi + \tan^2 P}\cos 2A + \frac{2\tan\Psi\tan P\cos\Delta}{\tan^2\Psi + \tan^2 P}\sin 2A\right) \quad (7)$$

For the light passing through the analyzer 607a, $P=\pi/4$, $A=A_1=0,\pi/2$, $\tan\Psi$ is the amplitude ratio of the p and s components of the light, and $\Delta$ is the phase difference between the p and s components. Light intensities $I(\pi/4,0)_{out}$ and $I(\pi/4, \pi/2)_{out}$ can be used to calculate the Fourier coefficient $$\alpha = \frac{\tan^2\Psi - 1}{\tan^2\Psi + 1},$$

and to further calculate the ellipsometric parameters $\tan\Psi$, that is:

$$\alpha = \frac{I(\pi/4, 0)_{out} - I(\pi/4, \pi/2)_{out}}{I(\pi/4, 0)_{out} + I(\pi/4, \pi/2)_{out}}, \quad (8)$$

$$\tan\Psi = \frac{I(\pi/4, 0)_{out}}{I(\pi/4, \pi/2)_{out}}$$

For the light passing through analyzer 607b, $P=\pi/4$, $A=A_2=\pm\pi/4$, which, from equation (7), results in light intensities $I(\pi/4,\pi/4)_{out}$ $I(\pi/4,-\pi/4)_{out}$. Moreover, $$\beta = \frac{2\tan\Psi\cos\Delta}{\tan^2\Psi + 1}$$

stands for the first-order Fourier coefficient. Therefore, $$\beta = \frac{I(\frac{\pi}{4}, \frac{\pi}{4})_{out} - I(\frac{\pi}{4}, -\frac{\pi}{4})_{out}}{I(\frac{\pi}{4}, \frac{\pi}{4})_{out} + I(\frac{\pi}{4}, -\frac{\pi}{4})_{out}} \quad (9)$$

Consistent with an embodiment, the Fourier coefficient can be calculated in advance. The variations of the Fourier coefficients $\alpha,\beta$ for different thicknesses are similar to those discussed for the first embodiment. When the incident angle $\theta$ is 75.55 degrees, the helium-neon laser outputs the incident light of 632.8 nm wavelength, the variations of the Fourier coefficients and of the ellipsometry parameters are similar to those shown in FIGS. 3a, 3b, 4a, and 4b.

The above-described embodiments show the measurement method when the fixed polarized azimuthal angle P and the fixed analyzer azimuthal angles $A_1$ and $A_2$ are all in the ideal state, that is $P=\pi/4, A_1=0,\pi/2, A_2=\pm\pi/4$, and when $\theta=75.55$ degrees. In the process of real measurement, due to the deviation in the measuring device and the light path, this condition is difficult to achieve. Thus, when there is a deviation in polarized azimuthal angle P, incident angle $\theta$, or the fixed analyzer azimuthal angles $A_1$ and $A_2$, a calibration action must be taken to determine the deviation in the fixed polarized azimuthal angle P and the incident angle $\theta$, and based on the determined fixed polarized azimuthal angle P and the incident angle $\theta$, to obtain the thickness of the target surface.

Figure 8:
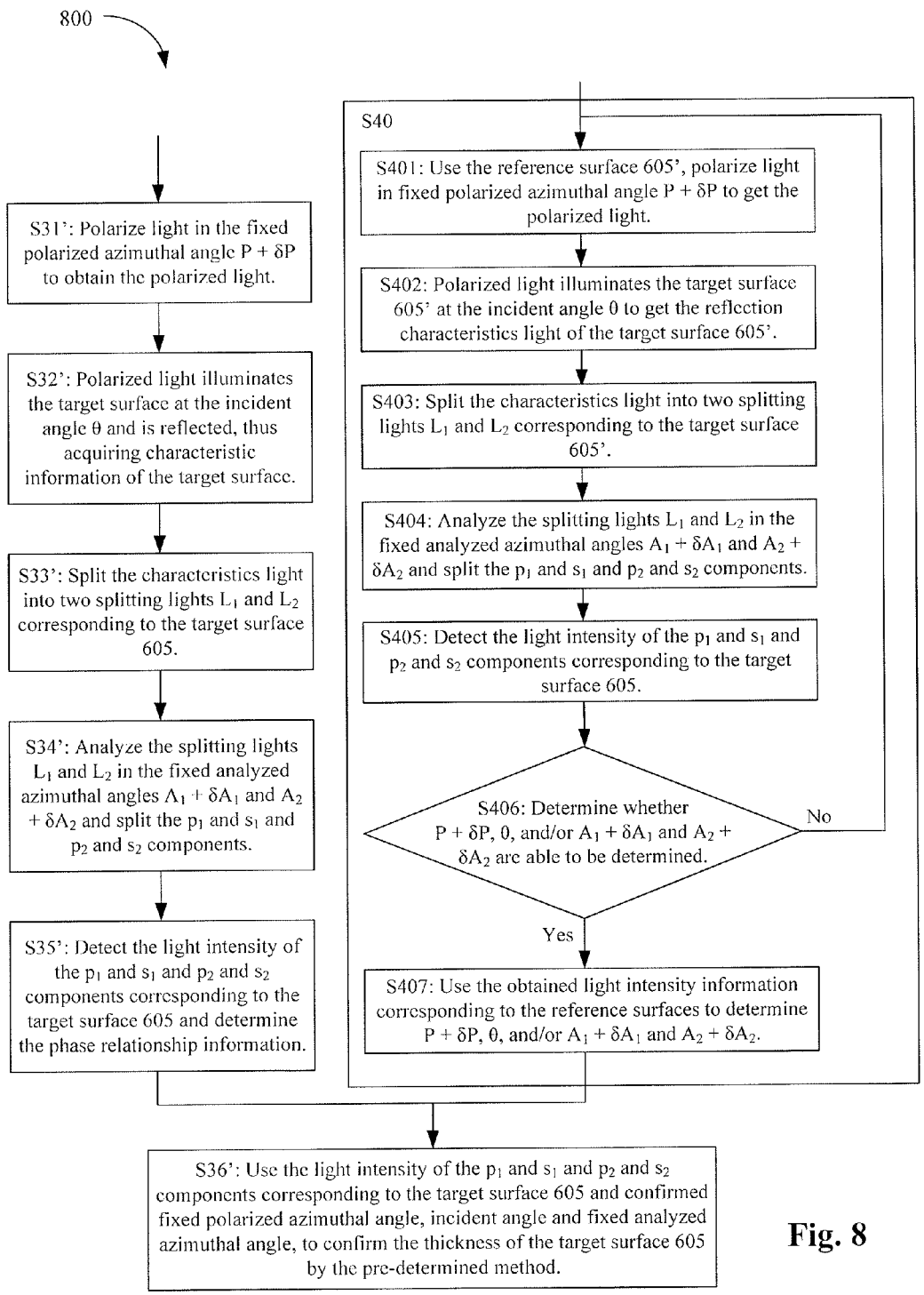
FIG. 8 illustrates a method of ellipsometric measurement, which includes calibration, in accordance with an embodiment.

To perform calibration, a method of measuring the thickness of the target surface, shown in FIG. 8, will also include steps S40. In steps S40, calibration is performed at the fixed polarizer azimuthal angle, the incident angle and the fixed-analyzer azimuthal angles $A_1$ and $A_2$, to obtain the actual value of the fixed polarizer azimuthal angle, the incident angle, and the fixed-analyzer azimuthal angle. The method of FIG. 8 also includes the above-described steps S31 to S35, labeled as steps S31' to S35', respectively, for determining light intensity information about the $p_1$, $s_1$, $p_2$, and $s_2$ components. Consequently, in step S36', based on the determined light intensity information about $p_1$ and $s_1$ components and $p_2$ and $s_2$ components, and also using the fixed polarizer azimuthal angle, the incident angle, and the fixed analyzer azimuthal angle, the thickness of the target surface can be determined.

Below is described the method of calibration for the polarized azimuthal angle, the analyzer azimuthal angle, and the incident angle. Based on the obtained azimuthal angles and on the obtained light intensities of the p and s components, the thickness is measured.

In FIG. 8, steps S40 show the calibration flow chart for the calibration method of the polarized azimuthal angle, the analyzer azimuthal angle, and the incident angle for the system shown in FIG. 6, which uses the surface reflection and light division technique. The calibration process in accordance with an embodiment is described below.

Before the calibration, first target surface 605 in FIG. 6 is replaced with reference surface 605' used for calibration. The calibration process works as follows. Supposing there is an azimuthal angle deviation between polarizer 603 and analyzers 607a and 607b, these angles are denoted as $P+\delta P$, $A_1+\delta A_1$ and $A_2+\delta A_2$, where $\delta P$ represents the deviation between the actual azimuthal angle P and the current theoretical value (e.g., π/4), and $\delta A_1$ and $\delta A_2$ respectively represent the deviations between the actual analyzer azimuthal angles $A_1$ and $A_2$ and the current theoretical value (e.g., 0 and π/2,π/4 and −π/4). The output light intensity is thus determined by the following equation:

$$I_{out}(P+\delta P, A+\delta A) = I_0 \begin{pmatrix} 1 + \\ \frac{\tan^2\Psi - \tan^2(P+\delta P)}{\tan^2\Psi + \tan^2(P+\delta P)}\cos 2(A+\delta A) + \\ \frac{2\tan\Psi\tan(P+\delta P)\cos\Delta}{\tan^2\Psi + \tan^2(P+\delta P)}\sin 2(A+\delta A) \end{pmatrix}$$

$$= \begin{pmatrix} 1 + \\ \alpha'\cos 2(A+\delta A) + \\ \beta'\sin 2(A+\delta A) \end{pmatrix}$$

$$= \begin{pmatrix} 1 + \\ (\alpha'\cos 2\delta A + \beta'\sin 2\delta A)\cos 2A + \\ (-\alpha'\sin 2\delta A + \beta'\cos 2\delta A)\sin 2A \end{pmatrix}$$

in which $$\alpha' = \frac{\tan^2\Psi - \tan^2(P+\delta P)}{\tan^2\Psi + \tan^2(P+\delta P)}$$

$$\beta' = \frac{2\tan\Psi\tan(P+\delta P)\cos\Delta}{\tan^2\Psi + \tan^2(P+\delta P)}$$

represents the theoretical Fourier coefficients, and $\Delta$ is the phase deviation between the p and s component for the characteristic light.

The theoretical value of the polarized azimuthal angle is P=π/4, its deviation is $\delta P$, the theoretical value of the analyzer 607a azimuthal angle $A_1$ is 00/90°, its deviation is $\delta A_1$, the theoretical value of the analyzer 607b azimuthal angle $A_2$ is 45°/−45°, and its deviation is $\delta A_1$. Therefore, the 4 light intensities are $$I_1 = I(0) = I_{01}(1+\alpha'\cos 2\delta A_1 + \beta'\sin 2\delta A_1)$$

$$I_2 = I(\pi/2) = I_{01}(1-\alpha'\cos 2\delta A_1 - \beta'\sin 2\delta A_1)$$

$$I_3 = I(\pi/4) = I_{02}(1-\alpha'\sin 2\delta A_2 + \beta'\cos 2\delta A_2)$$

$$I_4 = I(-\pi/4) = I_{02}(1+\alpha'\sin 2\delta A_2 - \beta'\cos 2\delta A_2)$$

After the normalization, the light intensities are determined as:

$$I'_1 = \frac{I_1}{I_{01}} = 1 + \alpha'\cos 2\delta A_1 + \beta'\sin 2\delta A_1 \quad (12)$$

$$I'_2 = \frac{I_2}{I_{01}} = 1 - \alpha'\cos 2\delta A_1 - \beta'\sin 2\delta A_1$$

$$I'_3 = \frac{I_3}{I_{02}} = 1 - \alpha'\sin 2\delta A_1 + \beta'\cos 2\delta A_1$$

$$I'_4 = \frac{I_4}{I_{02}} = 1 + \alpha'\sin 2\delta A_1 - \beta'\cos 2\delta A_1$$

Thus the objective function is, $$X(\vec{t}, \delta A_1, \delta A_2, \delta P, \vec{n}, \vec{k}, \lambda) = \sum_{i=1}^{4}\sum_{j=1}^{m}\left(I'_{ij} - I_{ij}^{theory}\right)^2 \quad (13)$$

in which $\vec{t}$ is the thickness of the surface, θ is the incident angle, $\delta P$ is the deviation of the polarizer azimuthal angle of polarizer 3, $\delta A_1$ is the deviation of the analyzer azimuthal angle for first analyzer 607a, $\delta A_2$ is the deviation of the analyzer azimuthal angle for second analyzer 607b, $\vec{n}$ is the refractive index of the reference surface, $\vec{k}$ is the extinction coefficient for the reference surface, and λ is the wavelength. In equation (13), $I'_{ij}$ is the normalized obtained light intensity and $I_{ij}^{theory}$ is the theoretically calculated light intensity. Further, in the sums in equation (13), the index i runs over the $p_1$ and $s_1$, $p_2$, and $s_2$ components, and the index j runs over various reference surfaces used for calibration.

Considering calibration equation (6), supposing that m reference surfaces with different known thicknesses are used for calibration, and that the wavelength of the used light is constant, then $\vec{n}$, $\vec{k}$ will also be constant. Thus, X has 4m variables. After removing the linear dependencies among related variables, there remains 2m variables that could be used. There are m+4 unknown variables including the variations $\delta P$, $\delta A_1$, $\delta A_2$, the incident angle θ, and m unknown thicknesses of the reference target surfaces. Using the basic calculating method, all the unknown parameters could be found only when 2m>m+4, that is m>4.

If one or more of polarizer 603 azimuthal angle P+$\delta P$, incident angle θ, and analyzer azimuthal angles $A_1+\delta A_1$ and $A_2+\delta A_2$ of the first and second analyzers 607a and 607b are known, then in the calibration step, the remaining variables can be calibrated. Since the number of unknown parameters is not high, then the required number of nonlinear equations and then the corresponding measurements on the reference surface time is reduced.

Above, the calibration and its supporting theory were described in accordance with the embodiments. The following detailed description describes the steps in the calibration process, in reference to FIGS. 8 and 6.

In step S401, polarizer 603 polarizes the light at the fixed polarized azimuthal angle P+$\delta P$ to generate the polarized light. In step S402, the polarized light illuminates the known reference surface 605' at the incident angle θ and is reflected off the surface as characteristic light. In step S404, light divider 606 divides the characteristics light to generate divided characteristic lights $L_1$ and $L_2$.

In step S404, analyzers 607a and 607b analyze characteristic lights $L_1$ and $L_2$ at fixed analyzed azimuthal angles $A_1+\delta A_1$ and $A_2+\delta A_2$, respectively, and analyze the $p_1$ and $s_1$, and $p_2$ and $s_2$, components of characteristic light $L_1$ and $L_2$.

In step S405, first and second detection-processing devices 608a and 608b detect the light intensity of the $p_1$ and $s_1$, and $p_2$ and $s_2$, components to obtain the light intensity information corresponding to reference surface 605'.

In equation (13), the variables include the thickness of the reference surface 605', the fixed polarizer azimuthal angle P+$\delta P$, the incident angle θ, the fixed analyzer azimuthal angle $A_1+\delta A_1$ and $A_2+\delta A_2$, the refractive index $\vec{n}$ of the reference surface 605', the light extinction coefficient $\vec{k}$ of the reference surface 605', and the wavelength λ. Using numerical approximation methods, assuming the light intensity of the detected p and s components and the square of the sum of the corresponding theoretical light intensity deviation to be determined, equation (13) provides a nonlinear equation for finding the thickness of the reference surface 605'.

In step S406, based on the relationship between the foresaid function number and the unknown parameters number, and based on the nonlinear equations corresponding to the reference surface 605', it is decided whether it is possible to determine all the unknown parameters, that is, the fixed polarized azimuthal angle P+$\delta P$, the incident angle θ, and the fixed analyzer azimuthal angles $A_1+\delta A_1$ and $A_2+\delta A_2$. If all of them could not be determined, the reference surface 605' will be replaced with another reference surface 605", and steps S401 to S406 will be repeated, until all the above-listed unknown parameters, that is, azimuthal angle parameters in the fixed polarized azimuthal angle P+IP, the incident angle θ and fixed analyzer azimuthal angles $A_1+\delta A_1$ and $A_2+\delta A_2$ can be determined by solving a plurality of nonlinear equations corresponding to the plurality of reference surfaces.

When it is possible to determine all the unknown azimuthal angle parameters according to one or more nonlinear equation (13) corresponding to one or more reference surfaces, the method moves to step S407. In step S407, based on one or more nonlinear equations corresponding to one or more reference surfaces, and using the relationships between the light intensity and surface characteristics information, derived from nonlinear optimization theory methods, all of the unknown parameters are determined, that is, the polarized azimuthal angle P+δP, the incident angle θ, and the fixed analyzer azimuthal angles $A_1+\delta A_1$ and $A_2+\delta A_2$ are determined. The calculating method could be the non-linear optimization method L-M, or could be any other method that could analyze the non-linear equations. The detailed calculation method depends on the available method. Consistent with an embodiment, calibration device 611 performs the calculating process.

Independent of the above-described steps S401 to S407 and steps S31 to S35, the calibration process also includes steps S31' to S35', as shown in FIG. 8. In steps S31' to S35', light intensities of the $p_1$ and $s_1$, $p_2$ and $s_2$, components are determined. It is noted that all the azimuthal angles, that is, the fixed polarized azimuthal angle is P+δP, the incident angle is θ, and the fixed analyzer azimuthal angles $A_1+\delta A_1$ and $A_2+\delta A_2$ are the same during the detecting process (steps S31'-S35') and the calibration process (steps S401-S407).

After determining the fixed polarized azimuthal angle P+δP, the incident angle θ, and the fixed analyzer azimuthal angles $A_1+\delta A_1$ and $A_2+\delta A_2$, in step S36', the known light parameters of the reference surface 605, that is, $\vec{n}$ and $\vec{k}$, and the detected azimuthal angle parameters, are inserted into equation (13), and using the L-M method the thickness is determined. In some embodiments, the calculating process is performed by the calculating device 609. Of course, other nonlinear functions could be used to determine this thickness, and the detailed determination method is not the focus of this disclosure.

In another embodiment, the ellipsometry measurement device stores one or more characteristic information and the ellipsometric parameters, such as P and A in a measurement database. Specifically, after the system calibration with above method, the obtained characteristic information of several target surfaces in the same conditions and their corresponding ellipsometric parameters are stored along with their corresponding relationship. In another embodiment, the corresponding relationship may be conducted from the outside. Then, when the characteristic information of the target surface by the electromagnetic waves, the azimuthal angle of the ellipsometric measurement remain constant, use the obtained corresponding ellipsometric parameters corresponding to the current target surface, based on the corresponding relationship between the ellipsometric parameters and the characteristic information pre-reserved in the database, the characteristic information could be obtained from this corresponding relationship by the obtained ellipsometric parameters.

The above description is a method, after using the target reflection change the ellipsometric state of the incident light, after the measurement for the characteristic information of the reflected characteristic light, of the characteristic information confirmation. This invention is not limited to the method of using the target reflection change the ellipsometric state of the incident light, besides, the using the target transmittance or diffraction change the ellipsometric state of the incident light, to get the corresponding characteristic light information then get the target characteristics.

Figure 9:
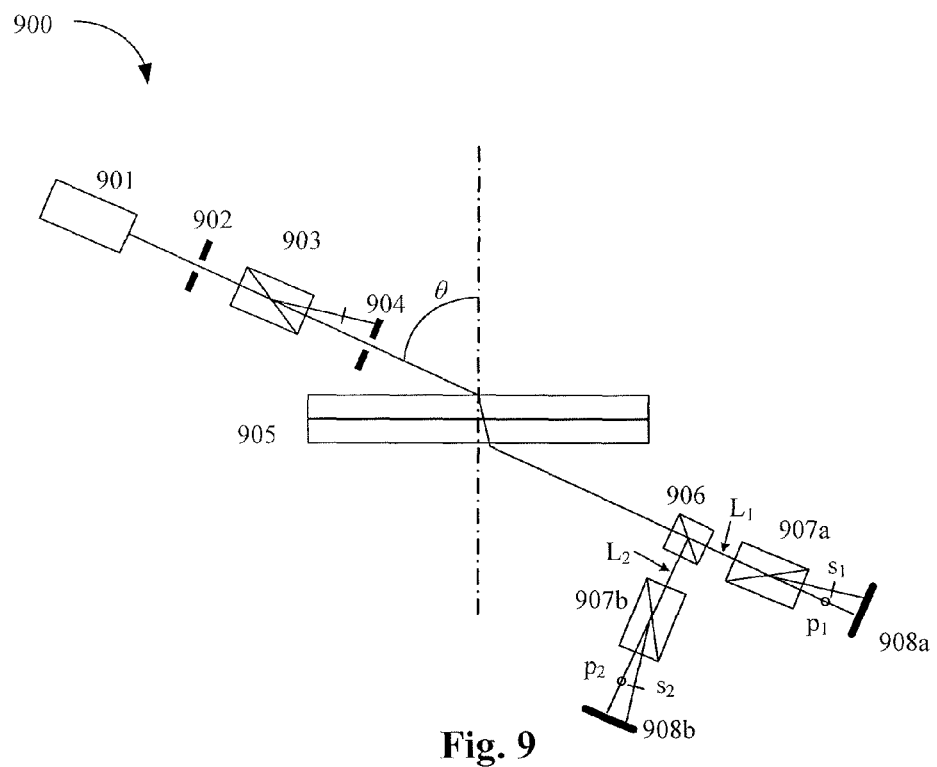
FIG. 9 shows a measurement system in accordance with an embodiment.

FIG. 9 shows a system in accordance with an embodiment. The system of FIG. 9 includes a light source 901, a first condenser hole 902, a polarizer 903 (at an azimuthal angle of 45 degrees), a second condenser hole 904, a target surface 905 (preferred to be the $SiO_2$ film), a light divider 906, a first analyzer device 907a (at an azimuthal angle of 0 degrees), and a first detection-processing device 908a. First detection-processing device 8a receives the output of first polarizer 907a, wherein the output is includes a p-polarized light component and an s-polarized light components, and detects the light intensity information of the s and p components and also detects the phase relationship between the s and p components. The system of FIG. 9 also includes a second analyzer device 907b (at an azimuthal angle of 45 degrees), and a second detection-processing device 908b. Second detection-processing device 908b receives the output of second polarizer 907b, wherein the output includes p polarized and s-polarized light components. Second detection-processing device 908b further detects the light intensity information of the s and p components and determines the phase relationship between the s and p components. Polarized light incident angle θ is near the target surface Brewster azimuthal angle. Further, in the system of FIG. 9, first and second detection-processing units 908a and 908b are connected to a computing device 909, which is not shown. The steps of the ellipsometry measurement method for determining the target surface thickness, and the fixed polarized azimuthal angles, the incident angle, or the calibration process are all similar with the previously described second embodiment. It is understood in this field that, the light divider 906, the analyzer 907b, and the detection-processing device 908b could be eliminated, in which case, the ellipsometric measurement steps for the target surface thickness and the calibration measurement steps will all be similar to the first embodiment, and will not be described again.

Figure 10:
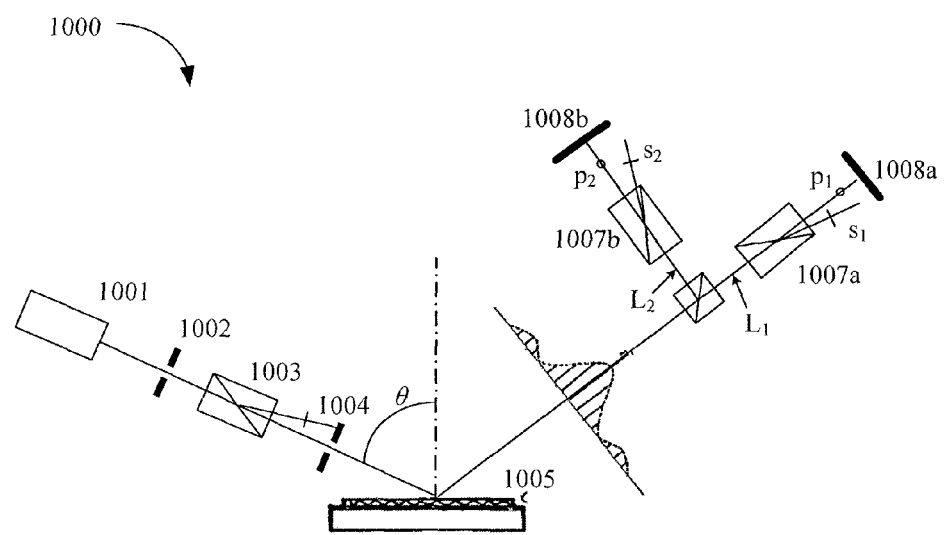
FIG. 10 shows a measurement system in accordance with an embodiment.

FIG. 10 shows a system consistent with an embodiment, using light division ellipsometry light road map of surface diffraction and light division techniques for the characteristic information identification by electromagnetic waves. Various sections of the system are similar to the corresponding sections of the system shown in FIG. 6. The system shown in FIG. 10 can be used in a manner similar to that described for the second embodiment. It is understood in this field that, light divider 1006, analyzer 1007b, and the detection-processing device 1008b could be eliminated, with the methods applied to system of FIG. 10 being similar to those described for the first embodiment.

It is understood that the disclosed embodiments are not limited to light reflection techniques, light transmission techniques, or light diffraction techniques. It is to be understood that this invention can be used to obtain polarized light characteristics via reflection, transmission, or diffraction, and then based on the obtained light characteristics to obtain the characteristic information of the target surface by electromagnetic waves. Using general techniques of this disclosure, the calibration and measurement steps of the ellipsometric measurement method can be improved. The methods of the invention are not limited of one of above-disclosed embodiments, and all kinds of variations or modifications could be applied to arrive at the scope of the following claims.

What is claimed is:

1. A method for measuring a value of a characteristic of a target surface based on ellipsometry techniques, the method comprising:

polarizing incident light via a polarizer adjusted at a polarizer azimuthal angle to generate polarized light;

illuminating via the polarized light the target surface at an incident angle to generate characteristic light;

analyzing the characteristic light via an analyzer at an analyzer azimuthal angle to obtain a p-component of the characteristic light and an s-component of the characteristic light;

detecting a first light intensity corresponding to the p-component and a second light intensity corresponding to the s-component;

detecting a phase relationship between the p-component and the s-component; and determining the value of the characteristic for the target surface based on a first relationship that is among the value of the characteristic, the first light intensity, the second light intensity, and the phase relationship, wherein the determining of the value of the characteristic for the target surface comprises:

calculating one or more values for one or more of (a) a Fourier coefficient or (b) an ellipsometry coefficient for the first light intensity and the second light intensity; and using a monotonic relationship between the value of the characteristic and the calculated one or more values to obtain the value of the characteristic, wherein the analyzing of the characteristic light, the detecting of the first light intensity and the second light intensity, the detecting of the phase relationship, and the determining of the value further comprise:

dividing the characteristic light via a divider into a plurality of divided characteristic lights;

for each of the plurality of divided characteristic lights:

obtaining, via one of a plurality of analyzers, a divided p-component and a divided s-component;

detecting a first divided light intensity corresponding to the divided p-component and a second divided light intensity corresponding to the divided s-component; and detecting a divided phase relationship between the divided p-component and the divided s-component; and determining the value of the characteristic for the target surface based on a second relationship that is among the value of the characteristic and the first divided light intensity, the second divided light intensity, and the divided phase relationship for each of the plurality of divided characteristic lights;

wherein a first one of the plurality of analyzers analyzes a first one of the plurality of divided characteristic lights at a first fixed analyzer azimuthal angle, and a second one of the plurality of analyzers analyzes a second one of the plurality of divided characteristic lights at a second fixed analyzer azimuthal angle, a difference between the first fixed analyzer azimuthal angle and the second fixed analyzer azimuthal angle being $\pi/4$.

2. The method of claim 1, further comprising calibrating to determine one or more of the polarizer azimuthal angle, the analyzer azimuthal angle, and the incident angle.

3. The method of claim 2, wherein the calibrating comprises:

polarizing the incident light via the polarizer adjusted at the polarizer azimuthal angle to generate polarized light;

illuminating via the polarized light a calibrating target surface at the incident angle to generate a calibrating characteristic light, wherein a value of the characteristic for the calibrating target surface is known;

analyzing the calibrating characteristic light via the analyzer at the analyzer azimuthal angle to obtain a calibrating p-component of the calibrating characteristic light and a calibrating s-component of the calibrating characteristic light;

detecting a first calibrating light intensity corresponding to the calibrating p-component and a second calibrating light intensity corresponding to the calibrating s-component;

detecting a calibrating phase relationship between the calibrating p-component and the calibrating s-component; and determining one or more of the polarizer azimuthal angle, the analyzer azimuthal angle, and the incident angle based on a third relationship that is among the value of the characteristic for the calibrating target surface, the first calibrating light intensity, the second calibrating light intensity, and the calibrating phase relationship.

4. The method of claim 1, further comprising calibrating to determine one or more of the polarizer azimuthal angle, a plurality of analyzer azimuthal angles each for one of the plurality of analyzers, and the incident light.

5. The method of claim 4, wherein the calibrating comprises:

polarizing the incident light via the polarizer adjusted at the polarizer azimuthal angle to generate polarized light;

illuminating via the polarized light a calibrating target surface at the incident angle to generate a calibrating characteristic light, wherein a value of the characteristic for the calibrating target surface is known;

dividing the calibrating characteristic light via the divider into a plurality of divided calibrating characteristic lights;

for each of the plurality of divided calibrating characteristic lights:

obtaining, via one of the plurality of analyzers, a divided calibrating p-component and a divided calibrating s-component;

detecting a first divided calibrating light intensity corresponding to the divided calibrating p-component and a second divided calibrating light intensity corresponding to the divided calibrating s-component;

detecting a divided calibrating phase relationship between the divided calibrating p-component and the divided calibrating s-component; and determining one or more of the polarizer azimuthal angle, the incident light, and the plurality of azimuthal angles for the plurality of analyzers based on a third relationship that is among the value of the characteristic for the calibrating target surface, the first divided calibrating light intensity, the second divided calibrating light intensity, and the divided calibrating phase relationship for each of the plurality of divided calibrating characteristic lights.

6. The method of claim 1, wherein calculating the one or more values comprises applying numerical approximation to derive the monotonic relationship.

7. The method of claim 1, wherein the characteristic light results from one or more of reflection, transmission, or diffraction of the polarized light by the target surface.

8. The method of claim 7, further comprising calibrating to determine one or more of the polarizer azimuthal angle, the analyzer azimuthal angle, and the incident angle.

9. The method of claim 8, wherein the calibrating comprises:
polarizing the incident light via the polarizer adjusted at the polarizer azimuthal angle to generate polarized light;
illuminating via the polarized light a calibrating target surface at the incident angle to generate a calibrating characteristic light, wherein a value of the characteristic for the calibrating target surface is known;
analyzing the calibrating characteristic light via the analyzer at the analyzer azimuthal angle to obtain a calibrating p-component of the calibrating characteristic light and a calibrating s-component of the calibrating characteristic light;
detecting a first calibrating light intensity corresponding to the calibrating p-component and a second calibrating light intensity corresponding to the calibrating s-component;
detecting a calibrating phase relationship between the calibrating p-component and the calibrating s-component; and
determining one or more of the polarizer azimuthal angle, the analyzer azimuthal angle, and the incident angle based on a third relationship that is among the value of the characteristic for the calibrating target surface, the first calibrating light intensity, the second calibrating light intensity, and the calibrating phase relationship.

10. A light division ellipsometry system for measuring a value of a characteristic of a target surface based on ellipsometry techniques, the system comprising:
a polarizer adjustable to a polarizer azimuthal angle to polarize incident light to generate polarized light to illuminate the target surface at an incident angle and generate characteristic light;
an analyzer adjustable to an analyzer azimuthal angle to analyze the characteristic light to obtain a p-component of the characteristic light and an s-component of the characteristic light;
an intensity detector to detect a first light intensity corresponding to the p-component and a second light intensity corresponding to the s-component;
a phase detector to detect a phase relationship between the p-component and the s-component; and
a processing device to determine the value of the characteristic for the target surface based on a first relationship that is among the value of the characteristic, the first light intensity, the second light intensity, and the phase relationship, wherein the processing device determines the value of the characteristic for the target surface by:
calculating one or more values for one or more of (a) a Fourier coefficient or (b) an ellipsometry coefficient for the first light intensity and the second light intensity; and
using a monotonic relationship between the value of the characteristic and the calculated one or more values to obtain the value of the characteristic,
wherein the system further comprises:
a divider to divide the characteristic light into a plurality of divided characteristic lights; and
for each of the plurality of divided characteristic lights:
one of a plurality of analyzers to obtain a divided p-component and a divided s-component;
a division light detector to detect a first divided light intensity corresponding to the divided p-component and a second divided light intensity corresponding to the divided s-component; and
a division phase detector to detect a divided phase relationship between the divided p-component and the divided s-component,
wherein the processing device determines the value of the characteristic based on a second relationship that is among the value of the characteristic and the first divided light intensity, the second divided light intensity, and the divided phase relationship for each of the plurality of divided characteristic lights; and
wherein a first one of the plurality of analyzers analyzes a first one of the plurality of divided characteristic lights at a first fixed analyzer azimuthal angle, and a second one of the plurality of analyzers analyzes a second one of the plurality of divided characteristic lights at a second fixed analyzer azimuthal angle, a difference between the first fixed analyzer azimuthal angle and the second fixed analyzer azimuthal angle being $\pi/4$.

11. The system of claim 10, wherein the characteristic light results from one or more of reflection, transmission, or diffraction of the polarized light by the target surface.

12. The system of claim 10, further comprising a calibrator to determine one or more of the polarizer azimuthal angle, the analyzer azimuthal angle, and the incident light.

13. The system of claim 12, wherein the calibrator determines one or more of the polarizer azimuthal angle, the analyzer azimuthal angle, and the incident angle based on a third relationship that is among a value of the characteristic for a calibrating target surface for which the value of the characteristic is known, a first calibrating light intensity, a second calibrating light intensity, and a calibrating phase relationship, wherein the first calibrating light intensity, the second calibrating light intensity, and the calibrating phase relationship are derived by applying the light division ellipsometry system to the calibrating target surface.

14. The system of claim 10, further comprising a calibrator to determine one or more of the polarizer azimuthal angle, a plurality of analyzer azimuthal angles each for one of the plurality of analyzers, and the incident light.

* * * * *